US 6,585,686 B2

(12) United States Patent
Cloud

(10) Patent No.: US 6,585,686 B2
(45) Date of Patent: Jul. 1, 2003

(54) METHOD OF COLLECTING FLUID WITH A BREASTPUMP MEMBRANE

(75) Inventor: Lori M. Cloud, Elk City, OK (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 09/848,604

(22) Filed: May 3, 2001

(65) Prior Publication Data

US 2002/0004642 A1 Jan. 10, 2002

Related U.S. Application Data

(60) Provisional application No. 60/202,008, filed on May 4, 2000, and provisional application No. 60/226,539, filed on Aug. 19, 2000.

(51) Int. Cl.⁷ ............................................. A61M 1/06
(52) U.S. Cl. ............................................. 604/74
(58) Field of Search ........................ 604/73, 74, 75, 604/76, 35, 36, 37, 38, 313, 314, 315, 346, 350, 500, 514

(56) References Cited

U.S. PATENT DOCUMENTS

| 141,005 A | | 7/1873 | Knapp |
| 155,720 A | | 10/1874 | Gray et al. |
| 897,289 A | | 9/1908 | Howell |
| 1,670,610 A | | 5/1928 | Colby |
| 4,799,922 A | * | 1/1989 | Beer et al. ............. 119/14.49 |
| 5,049,126 A | * | 9/1991 | Larsson ..................... 604/74 |
| 5,885,246 A | * | 3/1999 | Ford ........................ 604/74 |
| 6,090,065 A | * | 7/2000 | Giles ....................... 604/74 |

FOREIGN PATENT DOCUMENTS

EP     0 198 651     4/1986     ............ A61M/1/06

* cited by examiner

*Primary Examiner*—Manuel Mendez
*Assistant Examiner*—Mark K Han
(74) *Attorney, Agent, or Firm*—Baniak Pine & Gannon

(57) ABSTRACT

Method and apparatus for expressing and collecting mother's milk from a donor utilizing an adapted breastpump assembly. The method includes providing a breastpump assembly having a flexible membrane engaged upon a breast shield of the breastpump assembly. The breast shield is adapted for engagement with a donor's breast to facilitate the expression of mother's milk therefrom. A temporary fluid reservoir is established between the flexible membrane and a portion of the breast shield, the temporary fluid reservoir is provided to initially collect mother's milk upon expression from the donor's breast. This configuration enables the donor to assume a reclined position during the expression process and at least initially collect expressed mother's milk in the temporary fluid reservoir. Supplementarily, a bypass assembly maybe provided for conveying mother's milk from the temporary fluid reservoir to a collection receptacle. Utilizing the supplemental configuration, a donor mother need not raise from a reclined position to accommodate any stage of the expression procedure.

10 Claims, 2 Drawing Sheets

METHOD OF COLLECTING FLUID WITH A BREASTPUMP MEMBRANE

The present application claims priority from U.S. Provisional Patent Applications No. 60/202,008 (filed May 4, 2000) and 60/226,539 (filed Aug. 19, 2000).

TECHNICAL FIELD

The present invention relates generally to breastfeeding, and more specifically to an apparatus for preventing leakage during collection of mother's milk, and transferring the collected milk into an infant feeding container.

BACKGROUND OF THE INVENTION

Preparation for infant feeding may require the collection of the mother's milk in a container suitable for short term storage until an appropriate feeding time. There are occasions when it is inconvenient or not possible for mothers to breast feed their infants. At such times the availability of a quantity of mother's milk, in a suitable container, allows an infant the benefit of a familiar source of nourishment. A well known method for the collection of mother's milk utilizes a breast milk pump generally comprising a hood, or shield, that fits over the breast, a vacuum pump connected to the shield for intermittent production of negative pressure within the shield, and a receptacle or container for the expressed milk.

U.S. Pat. No. 5,720,722 describes a device and equipment used for breast milk collection, and includes other references to breastpumps. As illustrated, the collection apparatus of U.S. Pat. No. 5,720,722 includes a shield which covers the breast, becoming engaged to the surface of the breast by suction during intermittent operation of the vacuum pump. Between cycling of the suction, the shield may release from the surface of the breast. This potentially allows expressed milk to leak from the rim at the perimeter of the shield. The loss of milk may be more pronounced when the shield is made from a relatively rigid material that relies predominantly on formation of a seal by the forward edge of the rim of the shield. To avoid this occurrence, a user of a breastpump may lean slightly forward thereby causing expressed milk to drain from the funnel-shaped shield downwardly into the receiver.

Typically, there is no facility provided that accommodates a mother utilizing the breastpump while in the reclined position. This can be particularly important in a hospital setting after the birth of a child, because this is a time when the mother is normally going to be reclined in bed, or otherwise resting in a reclined position. Furthermore, there is typically no provision for temporary fluid storage in the volume of the shield itself as further facilitation of breast milk collection in a reclined position.

SUMMARY OF THE INVENTION

In view of the above described issues, among others, the present invention has been developed to provide enhancements and further benefits in breastpumps.

Conical or funnel shaped shields, known in the art and used with breast pump arrangements configured according to the present invention, will now allow collection of mother's milk in relative comfort, including reclining posture, without loss of liquid through leakage at the juncture of the arrangement and the surface of the breast. The inventive apparatus and method for leak-free milk collection, even in a reclined position, utilizes in one form a flexible sealing membrane that covers the mouth of the conical shield to provide increased and more consistent surface-to-surface contact between the breast and the incorporating assembly when the breast is positioned at the shield. Furthermore, the sealing membrane of this design provides accommodation for variations in breast size and shape.

In one contemplated embodiment, the flexible sealing membrane includes an aperture (also referred to herein as a hole, or access port) that is located approximately in the center of the membrane. It is through that aperture that milk passes into the shield's interior and then to the collection container (bottle) attached to the shield. Milk having passed through the aperture, may occupy a temporary reservoir formed between the inner surface of the flexible sealing membrane and the inner wall of the shield. In a reclined position, collected milk may be retained in the temporary reservoir until repositioning of the apparatus causes the milk to drain into the collection container (e.g., the mother sits up).

In another aspect of the present invention, a modification may be made to the wall of the conical shield which conveniently allows continuous transfer of milk from the temporary reservoir into the collection container. This feature obviates the need for the donor to periodically lean forward to drain the temporary reservoir. The modification is preferably made in the form of a bypass tube short-circuiting the normal milk delivery path (through the narrowed portion of the funnel-shaped shield structure) when the angular positioning of the collection assembly prevents natural flow of milk into the receiving container. When the adaptation of the bypass tube is included in the assembly, the mother can remain in, or assume, a reclined position for the entirety of the milk expression procedure.

Conical shields with flexible sealing membranes, according to the present invention allow convenient, comfortable, leak-free, hygienic collection of mother's milk. More specifically, the present invention provides a flexible membrane adapted for releasable engagement with a fluid collecting apparatus of a breastpump. The flexible membrane includes a flexible body having a sealing portion adapted to achieve releasable engagement upon a fluid collector of a breastpump assembly, and an access port adapted to abut a breast at an exterior side thereof. The access port and flexible body are configured to direct milk expressed from a donor's breast across the flexible membrane to an interior side thereof. In this way, the flexible body is configured to establish a milk retaining space between the interior side and the funnel-shaped shield of a conventionally designed breastpump assembly.

In an embodiment, a latex material was used for the flexible membrane. Specifically, a condom has been modified by cutting an aperture at the closed end and then stretched about the normally open mouth of the shield to establish the flexible sealing membrane, and the temporary holding reservoir. The condom required no further modification than noted.

The beneficial effects described above apply generally to the exemplary devices and mechanisms disclosed herein for a breastpump assembly. These and other advantages and attributes of the invention will be further understood upon consideration of the following detailed descriptions of certain embodiments, taken in conjunction with the drawings described below.

DETAILED DESCRIPTION OF EMBODIMENTS OF THE INVENTION

It is to be understood that the disclosed embodiments are merely exemplary of the invention that may be embodied in various and alternative forms. The drawings are not necessarily to scale, and some features may be exaggerated or minimized to show details of particular components. Therefore, specific structural and functional details disclosed herein are not to be interpreted as limiting, but merely illustrative and as a representative basis for teaching one skilled in the art to variously employ the present invention.

Figure 1:
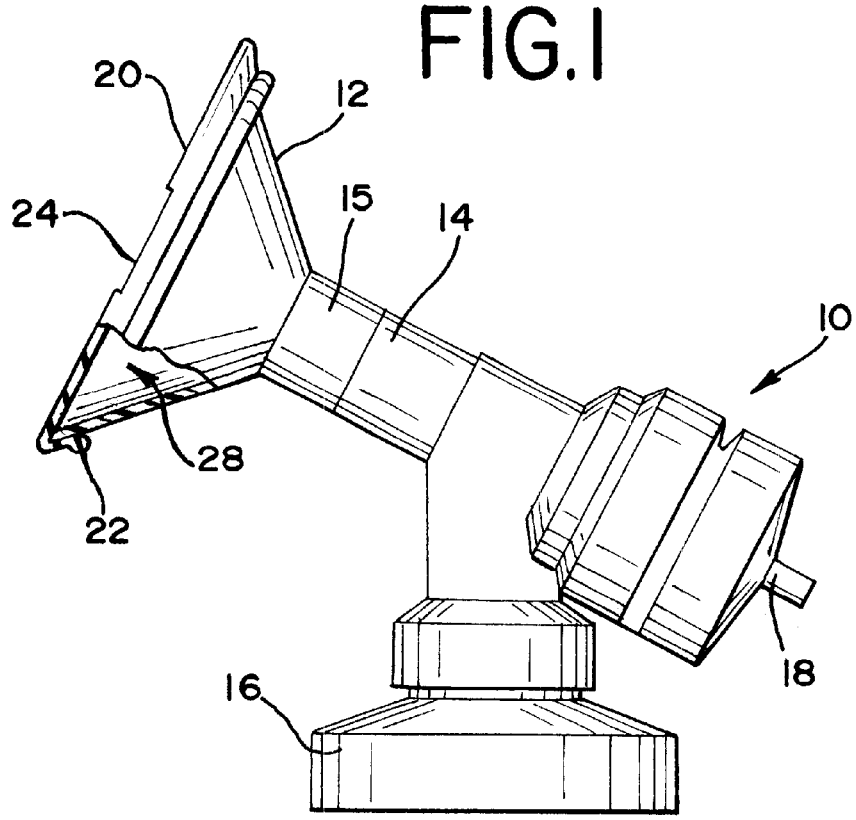
FIG. 1 is a side view of a breast milk collecting apparatus according to the present invention.
Figure 2:
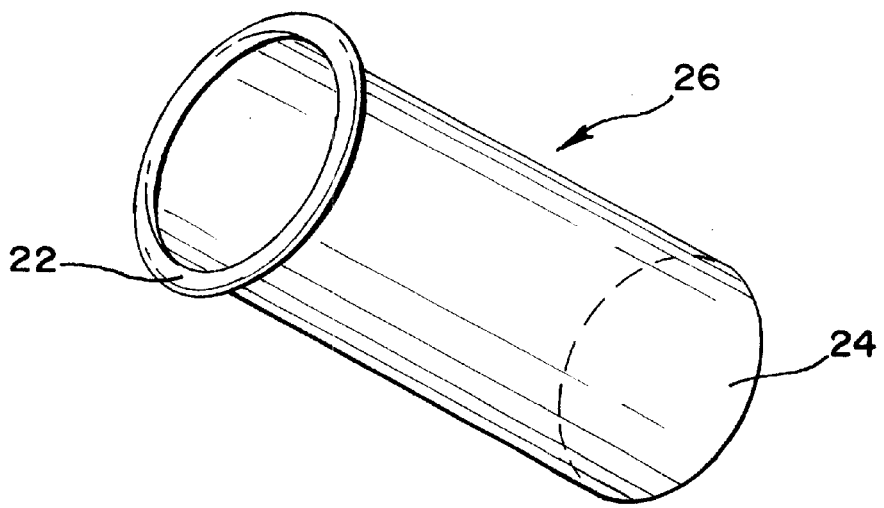
FIG. 2 is a perspective view of a flexible membrane in a pre-installation tubular configure as utilized in the breast-pump assembly of FIG. 1.

Referring to FIGS. 1–4, wherein like numbers refer to like parts throughout the several views, FIG. 1 shows a side view of a first embodiment of a fluid collection apparatus or assembly 10 according to the present invention. The primary purpose of the apparatus 10 is the collection of mother's milk. For this purpose, the apparatus 10 uses a conical or substantially funnel-shaped shield 12 of suitable size to extend beyond the nipple area of a human breast. Other shapes for the shield 12 can be used. The conical shield 12, also referred to herein as a fluid collector, is attached to a delivery tube (or tubular extension) 14 to guide the fluid, as it is collected, into a detachable reservoir (not shown, but a bottle, for example) associated with the delivery tube 14 by connecting cover, or collar, 16, which is usually threaded, much like a lid to a jar top. Milk collection is caused by intermittent reduction of the pressure inside the fluid collection apparatus using a suction pump connected to a suction outlet 18, as is well known in the art (see, for instance, U.S. Pat. No. 4,857,051).

To prevent loss of milk during the collection process, the widest dimension, or open mouth, of the conical shield 12 may be covered by a sealing flexible membrane 20 that has an access port 24 (see also FIG. 3) located approximately at the center of the flexible membrane 20. The sealing flexible membrane 20 has sufficient elasticity to allow it to stretch across the mouth of the conical shield 12, extending around its circumferential edge, and held in place by a thickened elastic band 22 that grips the outer surface of the conical shield 12. Before installation upon the funnel-shaped shield 12, the flexible member 20 may exemplarily take the form of a tubular structure 26 having the appearance shown in FIG. 2. From the illustration of FIG. 2, it may be appreciated that conventionally designed condoms may be modified according to the teachings contained herein for providing suitable flexible membranes for apparatus 10.

The tubular structure 26 has the thickened elastic band 22 at the open end and the opening for the access port 24 provided at the normally closed end. It will be appreciated that grasping the thickened elastic band 22 and stretching it evenly around the mouth of the conical shield 12 produces the flexible membrane 20 shown in FIG. 3.

Figure 3:
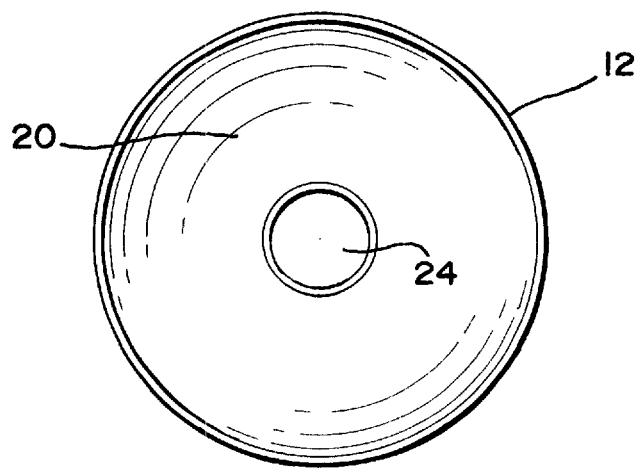
FIG. 3 shows a frontal elevational view of an installed flexible membrane of a breast milk collecting apparatus according to the present invention.

An end view of the mouth of the conical shield 12 appears in FIG. 3 showing the sealing flexible membrane 20 stretched over the mouth of the conical shield 12. The elasticity and flexibility of the sealing flexible membrane 20 allow it to follow the contours of a breast, inserted into the conical shield 12, to provide a surface-to-surface seal that prevents leakage of milk during the collection process. With a modicum of care in positioning the conical shield 12 of the fluid collection apparatus 10, there will be alignment between the nipple and the access port 24 in the flexible membrane 20 for direct transfer of milk into tube 14 then into the collection reservoir (not shown) that is attached to the connecting cover 16. Formation of a leak-free seal provides a closed volume, subject to reduced pressure, under the influence of a suction pump attached to the suction outlet 18.

FIG. 1 shows that before flowing into the delivery tube 14, a portion of the conical shield 12, shown in this side view as a V-shaped trough portion 28 but which is a three-dimensional crescent shaped sector, will collect fluid until the amount exceeds the volume of the trough portion 28. Having filled trough portion 28, milk will run down the delivery tube 14 into the reservoir attached to the connecting cover 16. The full contents of the reservoir created by trough portion 28 can be emptied by occasionally tilting the assembly 10 to an upright position as shown in FIG. 1. This causes the temporarily collected milk to drain down into the higher volume receiving container.

In an effort to minimize the volume of milk temporarily collected in the reservoir 28, the mother would typically adopt a relatively upright position, or otherwise tip the apparatus. This creates maximum flow to the container, but may be uncomfortable for the mother. At a minimum, it prevents collection of larger quantities of milk without filling the reservoir 28. This can have the negative effect of contributing to leakage between the membrane 20 and the shield 12. Furthermore, if the mother leans back sufficiently, a filled configuration of the reservoir 28 could result in back-flow out of the nipple receiving aperture.

Figure 4:
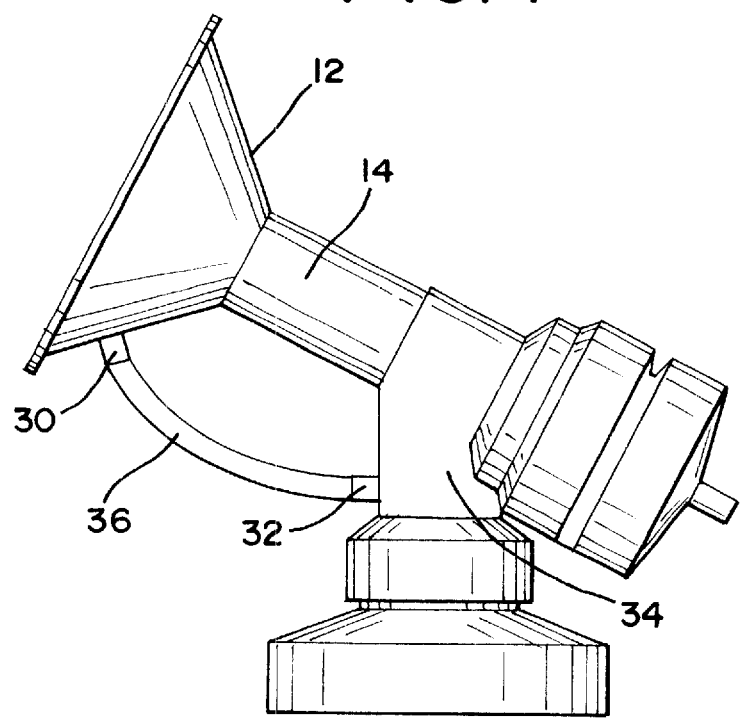
FIG. 4 shows a side view of an alternative embodiment of the present breastpump assembly, including a bypass tube that facilitates reclined expression of milk from a mother.

A solution for when the donor remains reclined during the milk expressing process is shown in FIG. 4. There, it is shown that a relief tube 30 is incorporated into the design of the shield 12 for emptying the portion 28. The relief at shield 12 may be provided merely in the form of an aperture connected directly to a receptacle. Using the relief tube 30 for present purposes, the tube 30 preferably connects to a relief inlet 32 formed at or near neck 34 between delivery tube 14 and connecting cover 16. A bypass tube, pipe or other conveyance 36 located between the relief tube 30 and the relief inlet 32 completes the supplemental channel that directs milk from portion 28 without going through the delivery tube 14. Collectively, or in various combinations, the bypass conveyance 36, the relief tube 30 and the relief inlet 32 can be referred to as a bypass assembly.

Using this alternative fluid collection apparatus, a mother may assume and maintain a reclined position before, during, and after use of the fluid collection apparatus 10 thereby enjoying greater convenience and comfort during the process of milk collection. Based on positioning and sizing of the relief tube 30, it is possible that the delivery tube 14 may be omitted in favor of the bypass tube or pipe 36. In either situation, that is whether the bypass configuration is provided singularly, or is in combination with a conventional delivery tube 14, the relief tube 30 is typically arranged as an aperture through shield 12, and is preferably located proximate to the open mouth of shield 12, where the flexible membrane 20 may be additionally installed.

To prevent any potential loss of suction through the bypass assembly, a one-way valve may be installed across the passage of the bypass and oriented so that when suction is applied, the valve closes and prevents the back-flow of air which might compromise the required vacuum. When suction is released, the valve opens and permits drainage of expressed milk from the reservoir 28 to the collection receptacle.

The present invention further takes the form of a method including the provision of the fluid collection apparatus 10 that incorporates at least the sealing flexible membrane 20. The V-shaped trough portion 28 is established for at least temporarily receiving expressed milk. The mother commences the process either in an upright or reclined position. If a bypass tube 36 is not provided, the mother may desire to at least sit up occasionally to move collected milk from the reservoir 28 into the permanent collection receptacle through the delivery tube 14. If a bypass tube 36 is provided, the mother will not be required to sit up at any time during the expression process. That is, not only may she be reclined when the process begins, but she may remain reclined throughout the procedure and even after its completion. The reason that the reclined position is uniformly accommodated is that the bypass tube facilitates substantially continuous draining of expressed milk from the reservoir area 28 to the permanent receiving container.

European Patent Application No. 0198651 A2 discloses a flexible diaphragm (2) associated with the cup member (1) of a vacuum apparatus as illustrated in FIG. 6 of that application. It is explained that the flexible diaphragm (2) is fitted over the mouth of the cup member and is maintained in position by one or more elastic rings which force the edge of the diaphragm sufficiently into the grooves so as to form an airtight connection between the outer wall of the cup and the diaphragm. What is absent form this disclosure, however, is the provision of the temporary collection reservoir as disclosed according to applicant's present invention. This is particularly evident from the description at page 5, line 17 of European Patent Application No. 0198651 A2 where it is explained that "the nipple will be drawn gently, but firmly, to the rear of the cup member" when the source of vacuum is applied.

Moreover, the method of collecting milk with the donor in a reclined position, including temporarily reservoiring expressed milk in the space between the membrane and the conical shield, is not disclosed, taught or suggested in European Patent Application No. 0198651 A2.

A fluid collection apparatus in the form of a breastpump, and its method of provision and utilization have been described. These and other variations, which will be appreciated by those skilled in the art, are within the intended scope of this invention as claimed below. As previously stated, detailed embodiments of the present invention are disclosed herein; however it is to be understood that the disclosed embodiments are merely exemplary of the invention that may be embodied in various forms.

I claim:

1. A breastpump assembly comprising:
   a conical breast shield having an opening adapted to receive a human breast; and
   a bypass conveyance for conveying mother's milk from a temporary fluid reservoir between the human breast and said conical breast shield to a collection receptacle.

2. A breastpump assembly comprising:
   a breast shield having an opening adapted to receive a human breast;
   a flexible membrane engaged over said breast shield, wherein a temporary fluid reservoir is thereby provided between an inner surface of said flexible membrane and an inner wall of said breast shield, and wherein said flexible membrane includes an access port configured to permit a nipple of the human breast to pass therethrough when the human breast is positioned against an exterior side of said flexible membrane such that expressed milk is collected in said temporary fluid reservoir;
   a collection receptacle; and
   a bypass conveyance for conveying the mother's milk from said temporary fluid reservoir to said collection receptacle.

3. The breastpump assembly according to claim 2, further comprising an aperture to said bypass conveyance at the temporary fluid reservoir.

4. The breastpump assembly according to claim 2, wherein said bypass conveyance further comprises a conduit extending from a bottom part of said temporary fluid reservoir and communicating with a collection container.

5. A method for expressing and collecting mother's milk even in a reclined position utilizing a breastpump assembly, said method comprising the steps of:
   providing a breastpump assembly having a flexible membrane engaged upon a mouth of a breast shield of the breastpump assembly, the breast shield sized and shaped for engagement with a breast to facilitate expression of the mother's milk therefrom;
   establishing a temporary fluid reservoir between the flexible membrane and a portion of the breast shield, the temporary fluid reservoir sized and shaped to initially permit collection of mother's milk upon expression from the breast; and thereby
   enabling the collection of some of the expressed mother's milk in the temporary fluid reservoir in the reclined position.

6. The method as recited in claim 5, said method further comprising:
   providing a bypass for conveying mother's milk from said temporary fluid reservoir to a collection receptacle.

7. The method as recited in claim 6, further comprising:
   using said breastpump assembly in a reclined position during an entire expression process.

8. The method as recited in claim 5, said method further comprising:
   constructing said flexible membrane to include:
   a flexible body having a sealing portion adapted to achieve releasable engagement upon said fluid collector; and
   an access port configured to abut a human breast at an exterior side of said flexible body, said access port and said flexible body configured to direct expressed milk across said flexible body to said temporary collection reservoir at an interior side of said flexible body.

9. A method for expressing mother's milk comprising:
   providing a breastpump assembly having a flexible membrane engaged upon a breast shield of the breastpump assembly, wherein a temporary fluid reservoir is provided between the flexible membrane and the breast shield; and
   assuming a reclined position during a period in the expression process, whereby expressed mother's milk is collected in the temporary fluid reservoir.

10. The method according to claim 1 further comprising:
    providing a bypass assembly for conveying mother's milk from the temporary fluid reservoir to a collection receptacle.

* * * * *